United States Patent
Archibong et al.

(10) Patent No.: US 11,926,846 B2
(45) Date of Patent: Mar. 12, 2024

(54) HYDROXYUREA TO ENHANCE SPERM CELLS

(71) Applicant: Meharry Medical College, Nashville, TN (US)

(72) Inventors: Anthony Archibong, Antioch, TN (US); James Hildreth, Nashville, TN (US); Letitia Lyons, Houston, TX (US); Shannon Roberson, Smyrna, TN (US)

(73) Assignee: Meharry Medical College, Nashville, TN (US)

( * ) Notice: Subject to any disclaimer, the term of this patent is extended or adjusted under 35 U.S.C. 154(b) by 1161 days.

(21) Appl. No.: 16/677,542

(22) Filed: Nov. 7, 2019

(65) Prior Publication Data

US 2020/0087619 A1    Mar. 19, 2020

Related U.S. Application Data

(63) Continuation of application No. PCT/US2018/031659, filed on May 8, 2018.

(60) Provisional application No. 62/503,131, filed on May 8, 2017.

(51) Int. Cl.
  *A61K 35/52*    (2015.01)
  *A01N 1/02*     (2006.01)
  *C12N 5/076*    (2010.01)

(52) U.S. Cl.
  CPC .......... *C12N 5/061* (2013.01); *A01N 1/0221* (2013.01); *A61K 35/52* (2013.01)

(58) Field of Classification Search
  None
  See application file for complete search history.

(56) References Cited

FOREIGN PATENT DOCUMENTS

| WO | 9317675 | 9/1993 |
|----|---------|--------|
| WO | 1998032440 | 7/1998 |
| WO | 1999047146 | 9/1999 |
| WO | 1999048526 | 9/1999 |
| WO | 2014043568 | 3/2014 |

OTHER PUBLICATIONS

The International Search Report and The Written Opinion of the International Searching Authority of PCT/US2018/031659, dated Sep. 25, 2018.
Pilcher et al., HIV in body fluids during primary HIV infection: implications for pathogenesis, treatment and public health, AIDS, 2001, vol. 15, No. 7, pp. 837-845.
Nicolini et al., CML Patients Show Sperm Alterations At Diagnosis That Are Not Improved on Tyrosine Kinase Inhibitor Treatment, Blood, 2012, vol. 120, No. 21, Abstract No. 1669.
Grigg, A., Effect of hydroxyurea on sperm count, motility and morphology in adult men with sickle cell or myeloproliferative disease, Internal Medicine Journal, 2007, vol. 37, No. 3, pp. 190-192.
Berthaut et al., Influence of sickle cell disease and treatment with hydroxyurea on sperm parameters and fertility of human males, Haematologica, 2008, vol. 93, No. 7, pp. 988-993.
Masood et al., Hydroxyurea therapy: a rare cause of reversible azoospermia, International Urology and Nephrology, 2007, vol. 39, No. 3, pp. 905-907.
Bachir et al., Prospective Comparison of Sperm Parameters in SCD Adult Patients Before and after a 6 Months Treatment with hydroxyurea (HU), Blood, 2012, vol. 120, No. 21, Abstract 242.
Cho et al., Successful Spouse Pregnancy of Male Patients with Severe Apalstic Anemia and Chronic Myelogenous Leukemia Using Spermatozoa Banked Prior to Bone Marrow Transplantation and Using the ICSI Procedure: Case Reports, Journal of Assisted Reproduction and Genetics, 2004, vol. 21, No. 2, pp. 59-61.
Smith-Whitley, K, Reproductive issues in sickle cell disease, Blood, 2014, vol. 124, No. 24, pp. 3538-3543.
Shin et al., Involvement of Germ Cell Apoptosis in the Induction of Testicular Toxicity Following Hydroxyurea Treatment, Toxicology and Applied Pharmacology, 1999, vol. 155, pp. 139-149.
Gao et al., Low levels of deoxynucleotides in peripheral blood lymphocytes: Astrategy to inhibit human immunodeficiency virus type 1 replication, Proc. Natl. Acad. Sci. USA, 1993, vol. 90, pp. 8925-8928.

*Primary Examiner* — Russell G Fiebig
(74) *Attorney, Agent, or Firm* — Bradley Arant Boult Cummings LLP; Phil Walker; Jessica L. Zurlo (57) ABSTRACT

A method of enhancing sperm fertility is described herein. The method includes contacting sperm with hydroxyurea. A composition is disclosed that includes sperm, hydroxyurea, and a buffer. Methods, kits, and compositions for enhancing sperm fertility are also provided.

10 Claims, 8 Drawing Sheets

HYDROXYUREA TO ENHANCE SPERM CELLS

CROSS-REFERENCE TO RELATED APPLICATIONS

This application is a continuation of and cites the priority of PCT/US2018/031659 filed 8 May 2018, and cited the priority of U.S. 62/503,131, filed May 8, 2017. PCT/US2018/031659 and U.S. 62/503,131 are incorporated herein by reference in their entireties.

STATEMENT REGARDING FEDERALLY SPONSORED RESEARCH OR DEVELOPMENT

This invention was made with government support under grant(s) awarded by the National Institutes of Health (NIH) Grant number: RO1 HD020419-1951 and IU54HD0431501-09 awarded by U.S. National Institutes of Health. The government has certain rights in the invention.

In this context "government" refers to the government of the United States of America.

BACKGROUND OF THE DISCLOSURE

Mature sperm cells (spermatozoa) are the male reproductive cells in sexual reproduction in animals, including humans. A sperm cell is a male gamete for fusion with a female gamete (ovum or egg cell). After fusion of the gametes, the resulting cell, a zygote, normally develops into an embryo.

Sperm has many characteristics that are important to fertility, including morphology and motility. Sperm motility, or the ability of sperm to swim properly to effectuate fertilization, is one such important characteristic of sperm in determining success of fertilization, both natural and artificial. In mammals, such as humans, effective sperm motility facilitates the passage of sperm through the cumulus oophorus and the zona pellucida, which surround the female reproductive egg cell, to complete fertilization of the female reproductive cell. In the case of internal fertilization, sperm motility is measured by the degree by which sperm cells move through the female reproductive tract to reach and fertilize an egg cell. In artificial insemination, sperm motility is measured by the ability of sperm cells to move through an aqueous solution to reach and fertilize an egg cell.

Human sperm cells have a flat, disc shaped head and a long flagellum, or tail. The tail flagellates, or whips, to propel normal sperm in a direction opposite of the tail at a rate of about 1-3 mm/minute. The flagellum is principally responsible for sperm motility.

Human sperm cells reach full motility (hyperactive motility or hyperactivity) as a result of environmental pH changes, such as in the uterine lumen after ejaculated sperm penetrates the ovulatory alkaline cervical mucus. During natural insemination, hyperactivity is typically triggered when the alkaline nature of seminal fluid, the medium of sperm during male ejaculation, is neutralized by the acidic vaginal environment. Hyperactivity is characterized by a non-directional vigorous motion pattern, which is a characteristic motion pattern of sperm that have acquired the ability to bind to and fertilize mature eggs.

Sperm motility may be measured by a variety of parameters, including by motility grade. Motility grade may be divided into four different classifications of active (i.e., non-passive) motility, which in order of decreasing motility, are: Grade a, Grade b, Grade c and Grade d, also known as motility IV, motility III, motility II and motility I, respectively. Grade a sperm motility is characterized by sperm that moves quickly and in a forward and straight direction opposite of the sperm tail. Grade b sperm motility is characterized by sperm that moves forwardly in a curved or indirect path. Grade c sperm motility is characterized by sperm that moves generally with tail movement but fails to move forward along a path. Grade d sperm motility is characterized by sperm that is immotile.

When sperm possess low sperm motility, fertilization is less likely to be achieved, as the sperm is not able to move effectively to reach an egg cell. In the context of assisted reproductive treatments, such as in vitro fertilization (IVF) and intrauterine insemination, a low sperm motility also decreases the likelihood of successful fertilization, as the low sperm motility results in sperm that are unable to effectively move through an aqueous environment to fertilize an egg cell.

Human sperm cells are environmentally sensitive, and as such, many environmental factors to which the human sperm cells are exposed may cause low or reduced sperm motility. Examples of activities in male subjects that result in such detrimental environmental factors include: tobacco use, marijuana use, alcohol consumption, anabolic steroid use, and use of testosterone supplements. Further detrimental factors to sperm motility in subjects include excessive stress, old age, excessive heat exposure to genitals, side effects of medication, and poor diet. As a large population of human male subjects have sperm that is affected by one or more of these detrimental factors, there is a need for technologies to enhance sperm motility.

SUMMARY

It has unexpectedly been discovered that hydroxyurea has positive effects on sperm motility, longevity and other factors related to sperm health, including in sperm of humans.

In a first aspect, a method of enhancing sperm motility is provided, comprising contacting hydroxyurea to sperm.

In a second aspect, a composition for enhancing sperm motility is provided that comprises an effective amount hydroxyurea and a buffer, such as human tubal fluid medium.

In a third aspect, a kit for enhancing sperm motility of sperm is provided. The kit includes hydroxyurea and a buffer, such as human tubal fluid medium or modified human tubal fluid medium.

In a fourth aspect, a plurality of treated sperm having enhanced motility are prepared by a process comprising contacting sperm with an effective amount of hydroxyurea.

In a fifth aspect, a method of suppressing human immunodeficiency virus ("HIV") in semen is provided. The method includes providing semen from a subject infected with the HIV and contacting the semen with hydroxyurea.

In a sixth aspect, a method of preventing HIV transmission from an HIV positive sperm donor is provided. The method includes providing semen from the HIV positive sperm donor, contacting the semen with hydroxyurea, and fertilizing an ovum with the sperm from the post-contacted semen.

In a seventh aspect, a method of increasing sperm longevity is provided that comprises providing sperm and contacting the sperm with an effective amount of hydroxyurea.

In an eighth aspect, a method of increasing a yield of post-thaw sperm sample after cryopreservation is provided.

The method includes providing a sample comprising a plurality of spermatozoa, contacting the spermatozoa with hydroxyurea, subjecting the spermatozoa to cryopreservation, and thawing the spermatozoa.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20%, preferably within 10%, and more preferably within 5% of a given value or range of values. For biological systems, the term "about" refers to an acceptable standard deviation of error, preferably not more than 2-fold of a given value. Numerical quantities in this detailed description are approximate unless stated otherwise, meaning that the term "about" or "approximately" can be inferred when not expressly stated.

The terms "individual," "subject," or "patient" as used herein refer to any animal, including mammals, such as mice, rats, other rodents, rabbits, dogs, cats, swine, cattle, sheep, horses, primates, and humans. The terms may specify male or female or both, or exclude male or female.

The term "spermatozoon" refers to a live male reproductive cell. The term "spermatozoa" refers to a plurality of live male reproductive cells. Unless required otherwise by context, the plural and singular forms are interchangeable. The term "sperm" is used as an abbreviation and refers to at least one spermatozoon. As used herein, sperm may be from a human male subject or an animal, including domesticated animals, such as bovines, equines, or swine.

Hydroxyurea ("HU"), also known as hydroxycarbamide, has a chemical formula of $CH_4N_2O_2$ and chemical structure of:

Surprisingly, it has presently been discovered that, among other things, hydroxyurea enhances the motility of sperm and has no adverse effects on sperm at beneficial concentrations. This is surprising as it was previously believed that HU was detrimental to male and female fertility.

A method of enhancing sperm motility may include contacting sperm with hydroxyurea. The sperm may be sperm that were isolated from semen from a human male or another animal such as bovine. The hydroxyurea may be contained in a suitable buffer, such as human tubal fluid medium or modified human tubal fluid medium, described further below. The hydroxyurea may be present in the buffer in an amount effective for enhancing sperm motility, such as in an amount of from 0.1 to 250 µg/mL, from 1 to 50 µg/mL, from 10 to 25 µg/mL, about 18 µg/mL, or any subvalue and/or subrange thereof. These concentrations may also reflect the concentration of hydroxyurea in the post-contacted sperm and buffer mixture. The method may increase progressive motility, i.e., linear movement from one point to another, of the sperm from sperm that are otherwise non-progressive, i.e., sperm that move but do not make forward progression.

In some embodiments, the enhanced motility comprises activated hyperactive motility, also known as hyperactivated sperm motility. Hyperactivated sperm motility is characterized by sperm that have a high amplitude, asymmetrical beating pattern of the flagellum. Hyperactivated sperm motility is more vigorous and short term than progressive motility. Biologically, hyperactivated sperm motility is important to enable sperm to traverse the egg outer investments prior to fertilizing the mature egg. The sperm motility may be enhanced prior to artificial insemination of the sperm. The method may include providing semen and isolating sperm from the semen. The method includes contacting the sperm with hydroxyurea to process the sperm. The buffer may comprise human tubal fluid medium or modified human tubal fluid medium. In an embodiment, the hydroxyurea processed sperm is incubated for a period of between 1 minute to 24 hours, 15 minutes to 3 hours, 30 minutes to 1.5 hours, about 1 hour, or any subrange and/or subvalue thereof.

As earlier provided, the sperm may be contacted with the hydroxyurea in a suitable buffer. Buffer is often used in procedures that require sperm washing, such as intrauterine insemination and in vitro fertilization. Sperm washing removes mucus (seminal plasma) and non-motile sperm from the semen. Thus, the hydroxyurea containing buffer serves to simultaneously increase sperm motility and to wash the sperm, which advantageously combines a washing buffer and hydroxyurea to increase motility in a single composition and step. The buffer may comprise hydroxyurea in any amount effective to produce a desired result, such as enhancing sperm motility or suppressing HIV, for example, of from 0.1 to 250 μg/mL, from 1 to 50 μg/mL, from 10 to 25 μg/mL, about 18 μg/mL, or any subrange or subvalue thereof. The buffer may be, for example, human tubal fluid ("HTF") medium or modified HTF medium. HTF comprises a sodium bicarbonate buffering system and may be utilized for uses requiring a carbon dioxide atmosphere during incubation. Modified HTF comprises a combined sodium bicarbonate and HEPES ([4-2(2-hydroxyethyl)-1-piperazineethanesulfonic acid]) buffer. Modified HTF provides maintenance of physiological pH (7.2 to 7.4) and is also appropriate for uses not requiring a carbon dioxide atmosphere during storage. Suitable examples of HTF medium or modified HTF medium include those that are commercially available from Irvine Scientific, Santa Ana, California. The sperm buffer solution may be incubated for a period sufficient to provide a measurable improvement in the motility (or other characteristics) of the sperm; in specific embodiments of the method, incubation is from 1 minute to 24 hours, 15 minutes to 3 hours, 30 minutes to 1.5 hours, about 1 hour, or any subrange or subvalue thereof.

In an embodiment of the method, a washing step is performed. The washing may include centrifuging sperm with a mixture of HTF-HEPES medium comprising 0.5% bovine serum albumin ("BSA") and separating and extracting the centrifuged sperm. The washing step may be performed before, simultaneously with, or after the sperm is processed with hydroxyurea.

A method of increasing sperm longevity is provided, comprising providing sperm and contacting the sperm with an effective amount of hydroxyurea to process the sperm. The effective amount of hydroxyurea may be from 0.1 to 250 μg/mL, from 1 to 50 μg/mL, from 10 to 25 μg/mL, about 18 μg/mL, or any subrange or subrange thereof. The effective amount of hydroxyurea may be up to a therapeutically safe amount of hydroxyurea. As the oral $LD_{50}$ of hydroxyurea in a single dose is 5780 mg/kg in rats, dividing by 1000 to calculate a rough maximum safe dose for humans, a maximum effective dose may be 5.78 mg/kg or less. While not impossible, it is unlikely that the hydroxyurea of the present disclosure would be administered orally. However, the maximum effective dose of 5.78 mg/kg based on the oral $LD_{50}$ in rats may be a useful guidepost in determining a maximum safe hydroxyurea level in humans, whether administered orally or via another route.

Without being bound by any particular hypothesis, it is believed that the increase in motility caused by hydroxyurea processing of sperm contributes to a longer longevity in sperm. Thus, sperm processed with hydroxyurea are able to be stored for a longer period of time and retain the ability to fertilize an egg cell as compared to sperm not processed with hydroxyurea.

In some embodiments, a method of increasing a yield of post-thaw sperm after sperm cryopreservation includes providing a sample comprising the sperm, contacting the sperm with hydroxyurea, subjecting the sperm to cryopreservation, and thawing the sperm. An increased yield of sperm means that a higher relative number of sperm are motile and capable of fertilization as compared to non-HU processed sperm. Thus, sperm processed with HU have a higher yield after cryopreservation and thawing than sperm not processed with HU. The hydroxyurea contacted sperm may also include any of several useful cryopreservative components, including one or more components such as glycerol, citrate, egg yolk, and antibacterial agents. Glycerol may be present at any concentration known in the art to preserve cellular viability upon freezing; examples of such concentrations include about 5-25% v/v, more specifically about 10-20% v/v, 12% v/v, and 15% v/v. Citrate and egg yolk can be used to reduce osmotic stress on the cells during penetration by glycerol. An example of a suitable cryopreservative component, a freezing buffer, is "Freezing Medium—TYB with Glycerol & Gentamicin," available commercially by Irvine Scientific of Santa Ana, California, which contains, among other ingredients, 20% egg yolk, 12% glycerol, and 10 μg/mL gentamicin sulfate. Antibiotics can be used to reduce the likelihood of microbial contamination of the sample. Such components may be used at concentrations that would be used in standard glycerol and glycerol-egg yolk cryopreservative. In an embodiment, the hydroxyurea is provided in a freezing buffer.

The method may include storing the mixture for a period of one day to 20 years, 30 days to 5 years, at least 2 weeks, at least a month, at least a year, or any subrange or subvalue thereof. In some embodiments of the method, the cryopreservation comprises freezing at a temperature sufficiently low for effective cryopreservation; for example, the cryopreservation may be conducted at about −10° C. or below; in further embodiments the composition is frozen at −40° C. or below; in still further embodiments the temperature is about −80°, −100°, −140°, −160°, −180°, or −190° C., and below.

In another aspect, hydroxyurea may be used in the manufacture of a composition for the prevention of HIV transmission or in the manufacture of a composition for enhancing sperm motility.

In an embodiment, the hydroxyurea of the present disclosure enhances a motility grade of sperm. For example, hydroxyurea treatment may enhance the sperm motility of sperm having Grade c sperm motility to Grade a sperm motility. Hydroxyurea treatment may enhance sperm motility of sperm having Grade b sperm motility to Grade a sperm motility. Hydroxyurea treatment may enhance sperm motility of sperm having Grade c sperm motility to Grade b sperm motility.

Advantageously, hydroxyurea may be used to enhance sperm motility prior to artificial insemination. As hydroxyurea activates, or induces, hyperactive motility in sperm, hydroxyurea may be used to induce hyperactive motility in sperm during an artificial insemination process to increase likelihood of successful fertilization of an egg cell, such as an egg cell of a human female or a domesticated female animal, such as a female swine or bovine.

In an embodiment, hydroxyurea may be used to activate hyperactive motility in sperm in an ex vivo fertilization method, such as an in vitro fertilization method.

In another embodiment, a composition comprises sperm, an effective amount of hydroxyurea, and a buffer. The buffer may be any buffer that is suitable as a medium for viable sperm, such as HTF or modified HTF medium. The hydroxyurea may be present in the buffer in an amount of from 0.1 to 250 μg/mL, from 1 to 50 μg/mL, from 10 to 25 μg/mL, about 18 μg/mL, or any subrange and/or subvalue thereof.

In some embodiments, a kit for enhancing motility of sperm comprises an effective amount of hydroxyurea and a buffer. The buffer may be any buffer disclosed as suitable above. The kit may consist essentially of, or consist solely of, the effective amount of hydroxyurea and the buffer, such as HTF or modified HTF. The hydroxyurea may be provided in the buffer or separately to be mixed later. The hydroxyurea may be present in the buffer in any effective amount, for example from 0.1 to 250 µg/mL, from 1 to 50 µg/mL, from 10 to 25 µg/mL, about 18 µg/mL, or any subrange and/or subvalue thereof. The hydroxyurea and the buffer may be contained separately, or together, in a suitable container or containers in the kit.

In an embodiment, a plurality of sperm with significantly enhanced motility are provided that are the product of a process comprising providing sperm and contacting the sperm with hydroxyurea. The significantly enhanced motility may be enhanced by at least 10%, at least 20%, at least 50%, or at least 75% or about 80%. The significantly enhanced motility may be enhanced by from 10% to 200%, from 25% to 150%, from 50% to 100%, or from 70% to 90%. The significantly enhanced motility may be significantly enhanced activation of hyperactive motility. The significantly enhanced motility refers to the number of sperm cells in an HU treated sample able to fertilize an egg as compared to those in a non-HU treated sample.

In another embodiment, hydroxyurea may be used in a method to process a semen sample infected with the human immunodeficiency virus ("HIV"). The method may be an ex vivo process, which has the advantages of more controlled processing conditions and lack of possible side effects in the donor. The processing of the sperm may comprise suppressing HIV replication, expression, and/or activation in semen or semen sample. In some embodiments, the processing prevents HIV transmission between an HIV positive spermatozoon donor and a spermatozoa recipient. The recipient may be, for example, a human female subject having an egg cell inseminated by the sperm of the HIV positive sperm donor.

Hydroxyurea may be added to a medium containing semen from a subject infected with the HIV. The hydroxyurea may be added to process the sperm prior to insemination of the sperm recipient. Hydroxyurea may be present in the culture medium in any amount effective to suppress HIV in semen, such as from 0.1 mM to 10 mM, from 0.5 mM to 5 mM, from 0.75 mM to 2.5 MM, or 1.0 mM, or any subrange and/or subvalue thereof. The sperm may be incubated in the HU containing medium (i.e., left in contact with the hydroxyurea) for a period sufficient to have a beneficial effect, for example, from 1 minute to 24 hours, from 15 minutes to 3 hours, from 30 minutes to 1.5 hours, about 1 hour, or any subrange and/or subvalue thereof. Without being bound by any particular hypothetical model, it is believed that HU depletes deoxyribonucleotide triphosphate ("dNTP") in stimulated peripheral blood lymphocytes ("PBLs"). The depletion of dNTP significantly reduces the rate of HIV-1 (the most widespread strain of HIV) DNA synthesis and inhibits the completion of viral DNA synthesis in phytohemagglutinin (PHA)-stimulated PBLs.

In an embodiment, hydroxyurea of the present disclosure is used in a method of deactivating HIV in semen prior to freezing, or cryopreservation, of HIV infected semen. In another embodiment, hydroxyurea of the present disclosure is used in a method of deactivating HIV in semen during an infertility treatment. In some embodiments, the hydroxyurea of the present disclosure is used for deactivating HIV in semen prior to motile sperm isolation from semen prior to sperm preparation for artificial insemination or in vitro fertilization.

In any of the embodiments disclosed herein, the hydroxyurea may be optionally separated, or washed, from the post-contacted sperm or semen with hydroxyurea. This optional separating step may be advantageous, as direct human exposure to hydroxyurea may have harmful side effects. Any suitable means of separating the hydroxyurea from the post-contacted sperm may be used, such as column chromatography, filtration, or differential centrifugation.

Working Example 1

Human sperm was processed with HU to show enhanced motility over human sperm not processed with HU. Normal human semen was collected in 15 mL conical centrifuge tubes. Highly motile (i.e., Grade a) sperm were isolated and collected from the semen. The isolated highly motile sperm were washed in an HTF medium (HTF-HEPES; pH 7.4) containing 0.5% Bovine Serum Albumin ("BSA") by centrifugation and suspended in bicarbonate (25 mM)-buffered HTF containing 0.5% (5 mg/ml) BSA (36; pH 7.4). Subsequently, each sperm suspension was incubated at 37° C. in an atmosphere of 5.0% $CO_2$ in humidified air until aliquoted into the different treatment groups: a control group and a hydroxyurea processed group.

The control group was cultured in HTF-buffer containing 0 µg HU/mL at 37° C. in an atmosphere of 5.0% $CO_2$ in humidified air for 24 hours. After the 24 hour culture, the control sperm were evaluated for pattern and degree of motility.

The hydroxyurea processed group was cultured in HTF-buffer containing 18 µg HU/mL at 37° C. in an atmosphere of 5.0% $CO_2$ in humidified air for 24 hours. After the 24 hour culture, the hydroxyurea processed sperm were evaluated for pattern and degree of motility. The resulting overall sperm motility (progressively motile spermatozoa [spermatozoa that swim mostly in a straight line or in very large circles]+hyperactively motile spermatozoa [spermatozoa that exhibit higher amplitude of lateral head displacement, and lower frequency of progressive motility]) as the number of motile spermatozoa in a hundred cells was viewed with a phase contrast microscope and counted with a laboratory counter. The percentage of motile spermatozoa was calculated by multiplying the ratio of motile to 100 spermatozoa counted by 100. The non-hydroxyurea treated group (control) had an overall percentage motility value of 75.4 with a standard error of ±8.6%, while the hydroxyurea processed group had a sperm motility of 79.0 with a standard error of ±7.0%.

Measuring, as described above, only the resulting progressive sperm motility, the control group had a motility of 51.7±10.2%, while the hydroxyurea processed group had a sperm motility of 37.7 with a standard error of +8.4%. The progressive motility of the control group sperm was higher (P<0.001; based on paired t-test comparison) than the progressive motility of the hydroxyurea processed group sperm. Surprisingly, measuring only the resulting hyperactive motility, as described above, the control group had a hyperactive motility of 23.0 with a standard error of ±6.4%, while the hydroxyurea processed group had a hyperactive motility of 41.3 with a standard error of ±5.3%. The hydroxyurea processed group possessed significantly higher (P<0.001; based on paired t-test comparison) hyperactive motile spermatozoa compared to spermatozoa in the control group. These results indicate that hydroxyurea stimulates hyperactive motility in sperm, thus increasing the number of sperm that have acquired the ability to bind to and fertilize mature egg cells. On the other hand, most of the sperm cells in the control buffer remained in a progressive motility state (motility pattern observed among sperm cells that have not acquired the ability to fertilize mature eggs). These findings are clinically significant, as progressive sperm motility is a determinant of ability of spermatozoa to penetrate cervical mucus on towards migration to the fertilization site (fallopian tubes), while that for hyperactive sperm motility (capacitation) is the motion pattern characteristic of spermatozoa that have attained the ability to fertilize mature eggs.

Working Example 2

Human sperm was processed with HU to show that in the context of preventing HIV transmission, HU has no significant negative side effects on overall sperm motility. This result is surprising, as it had been previously believed that HU was an unsuitable agent to suppress HIV replication and/or activation in sperm, or to reduce the risk of HIV transmission via HU treatment of reproductive cells, due to adverse effects of HU on reproductive cells, such as human sperm and human egg cells, including adverse effects on overall sperm motility and survival.

Normal human semen was collected in 15 mL conical centrifuge tubes. Highly motile (i.e., Grade a) sperm were isolated and collected from the semen. The isolated highly motile sperm were washed in HTF medium containing 0.5% BSA (HTF-HEPES; pH 7.4) by centrifugation and suspended in bicarbonate (25 mM)-buffered HTF containing 0.5% (5 mg/ml) BSA (36; pH 7.4). Subsequently, each sperm suspension was incubated at 37° C. in an atmosphere of 5.0% $CO_2$ in humidified air until aliquoted into the different treatment groups: a control group and a hydroxyurea processed group.

The control group was cultured in HTF-buffer containing 0 μg HU/mL at 37° C. in an atmosphere of 5.0% $CO_2$ in humidified air for 24 hours. After the 24 hour culture, the control sperm were evaluated for pattern and degree of motility.

The hydroxyurea processed groups were cultured in HTF-buffer in two groups containing different concentrations of HU: (1) 1.0 mM HU and (2) 2.0 mM HU. The groups were cultured at 37° C. in an atmosphere of 5.0% $CO_2$ in humidified air for 24 hours. After the 24 hour culture, the hydroxyurea processed sperm were evaluated for pattern and degree of motility.

Surprisingly, measuring overall motility, the HU treated groups had similar overall motility measurements as compared to the control group. The control group had an overall motility of 70.3 with a standard error of ±3.6. The 1.0 mM HU-treated group had an overall motility of 66.6 with a standard error of ±2.6. The 2.0 mM HU treated group had an overall motility of 68.3 with a standard error of ±4.0. These results are surprising, as previously it was thought that HU was damaging to reproductive cells such as sperm and would reduce sperm motility. Thus, it had been previously believed that HU was an unsuitable agent to suppress HIV replication and/or activation in semen, or to reduce the risk of HIV transmission, via HU treatment of reproductive cells.

Working Example 3

Human sperm was processed with HU to show that HU is beneficial for maintaining and preserving spermatozoa subjected to cryopreservation. This result was surprising, as HU processing, or contacting of sperm, showed that hydroxyurea processed sperm is superior for maintaining spermatozoa in a freezing medium for 24 hours when compared to sperm that has not been processed or contacted with hydroxyurea.

Post semen analysis was conducted of discarded and de-identified semen samples from Ovation Fertility Center that met the World Health Organization (WHO) criteria for normal semen samples. Those semen samples that met the WHO criteria for normal were divided into two halves. One half was subjected to freezing with TEST-Yolk buffer (freezing buffer [FB]; Irvine Scientific, CA) containing 12% glycerol as cryoprotectant (control group). The remaining half of each sample was frozen with experimental freezing buffer composed of FB+HU (Sigma Aldridge, St. Louis; treatment group). Both control and experimental buffers were added on a 1:1 ratio to respective semen samples (v/v) in a dropwise manner. The final glycerol concentration in the semen+FB was 6%, and the final HU concentration in semen+experimental freezing buffer was 1 μM to use a concentration of HU that is effective in inhibiting HIV replication. Pre-freeze sperm motility was determined for each sample prior to initiating the cooling step of the freezing procedure. Samples in the control and treatment group were cooled for 24 hours to slow the HU-induced vigorously motile cells in the treatment group. Subsequently, post cooling motility was determined prior to liquid nitrogen vapor phase freezing for 30 minutes before being stored immersed in liquid nitrogen (LN) for at least 24 hours before being thawed for analysis. Samples were thawed at room temperature for 35 minutes prior to motility analysis.

The results, as shown in Table 1, below, indicate that supplementation of freezing medium with HU maintained 76-84% motility of the initial population of motile spermatozoa (pre-freeze) which is significantly higher than that observed for spermatozoa in the control group (28-45% of pre-freeze population). Furthermore, longevity was higher among post-thaw spermatozoa frozen in the treatment (HU) group versus those in the control group.

TABLE 1

| Sample No. | CONTROL Pre-cool Motility (%) | CONTROL Post-cool Motility (%) | CONTROL Post-cool Motility Relative to Pre-cool Motility (Survival of cooling process; %) | Experimental Pre-cool Motility (%) | Experimental Post-cool Motility (%) | Experimental Post-cool Motility Relative to Pre-cool Motility (Survival of cooling process; %) |
|---|---|---|---|---|---|---|
| 1 | 47 | 27 | 57.4 | 47 | 40 | 85.1 |
| 2 | 62 | 29 | 47.8 | 62 | 37 | 59.7 |
| 3 | 44 | 18 | 40.9 | 44 | 29 | 65.9 |
| 4 | 63 | 26 | 41.3 | 63 | 36 | 57.1 |
| 5 | 54 | 22 | 40.7 | 54 | 40 | 74.1 |
| 6 | 38 | 29 | 76.3 | 38 | 33 | 86.8 |
| 7 | 79 | 40 | 50.6 | 79 | 59 | 74.7 |

As can be seen in Table 1, above, HU is highly effective at preserving, maintaining motility in, and maintaining survival of, motile spermatozoa that are subsequently subjected to cryopreservation as compared to non-HU treated motile spermatozoa. Indeed, in every one of the samples tested above, HU treatment increased yield of motile spermatozoa as compared to non-HU treated motile spermatozoa. The mean of the control post-cool motility relative to post-cool motility (survival of cooling process in percentage) of the seven samples was found to be 50.71 with a standard error of ±4.86. Advantageously, the mean of the post-cool motility relative to post cool motility (survival of cooling process in percentage) of the seven HU treated samples was found to be 71.91 with a standard error of ±4.39.

Figure 1A:
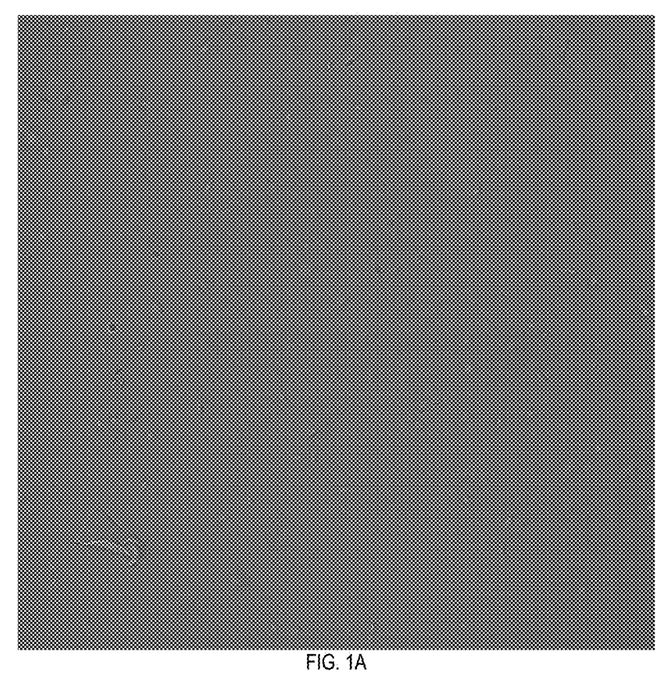
FIGS. 1A-1H depict photographs taken over about 9 seconds showing sperm not processed with hydroxyurea (control).
Figure 1B:
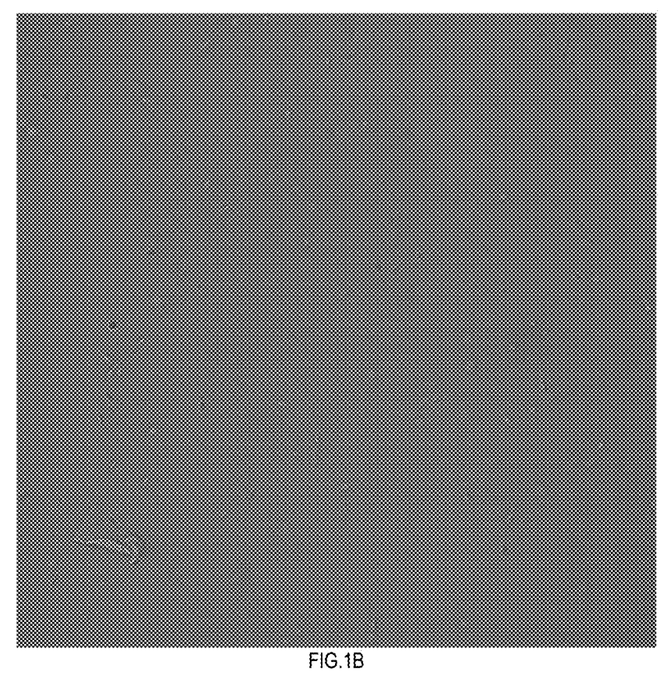
Figure 1C:
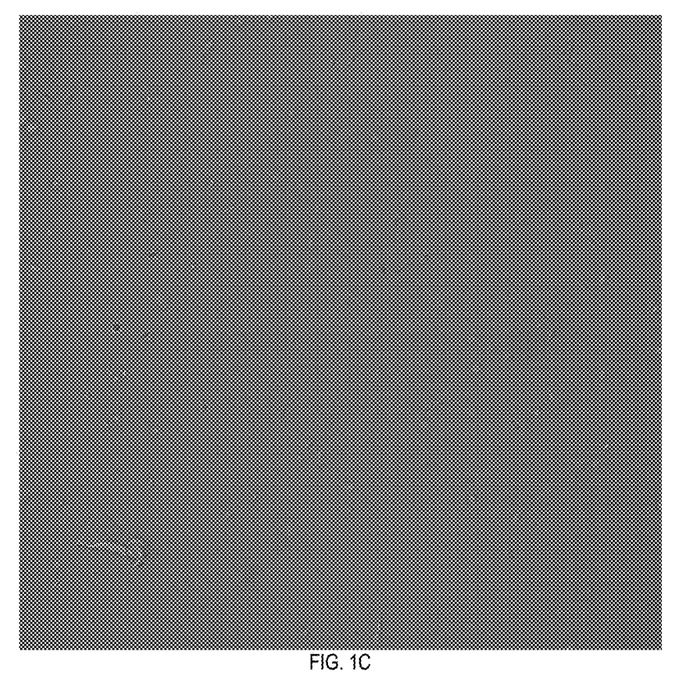
Figure 1D:
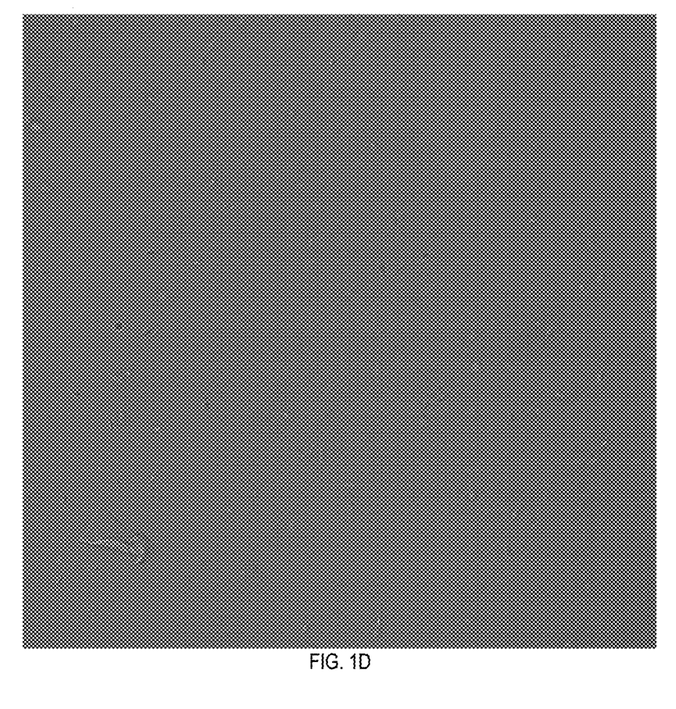
Figure 1E:
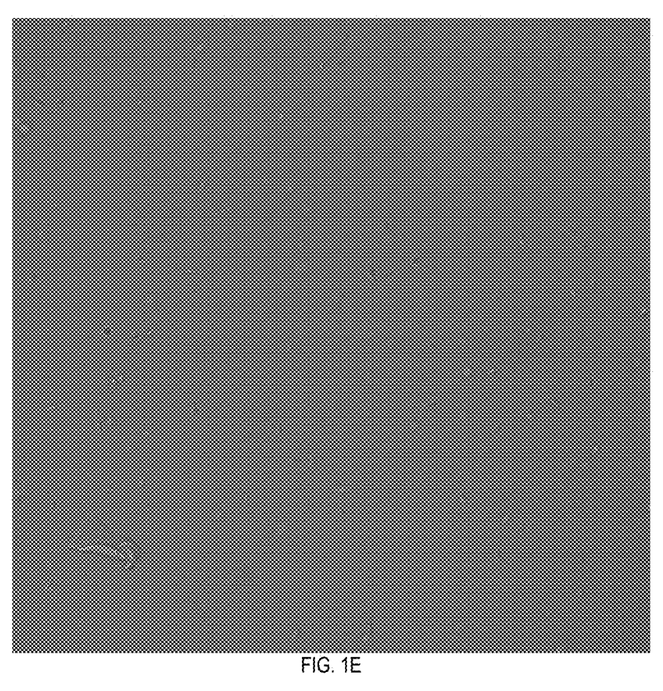
Figure 1F:
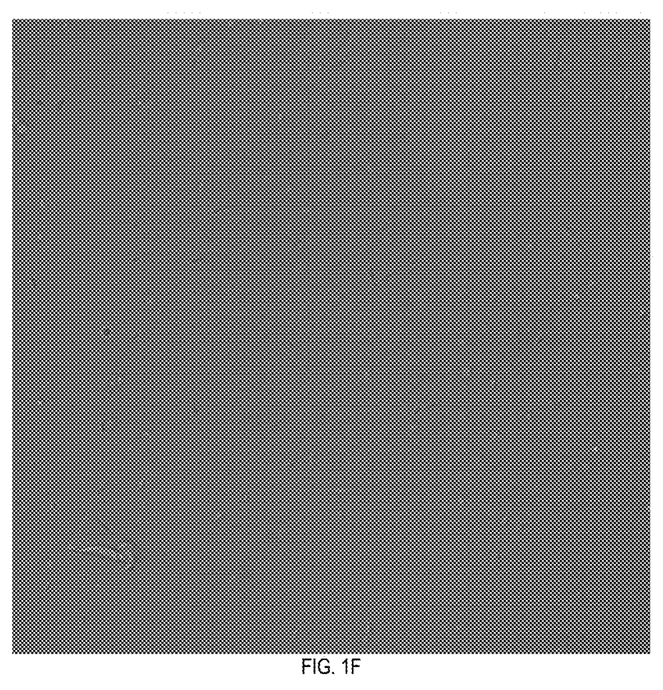
Figure 1G:
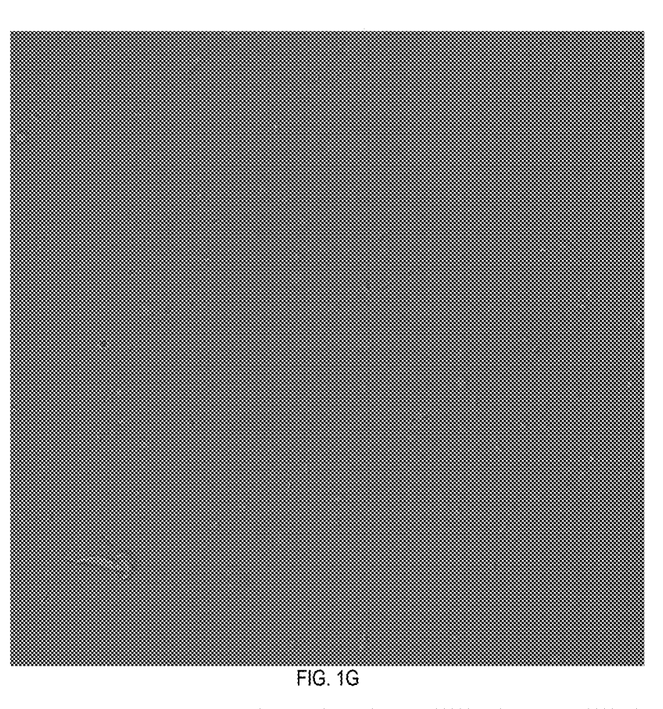
Figure 1H:
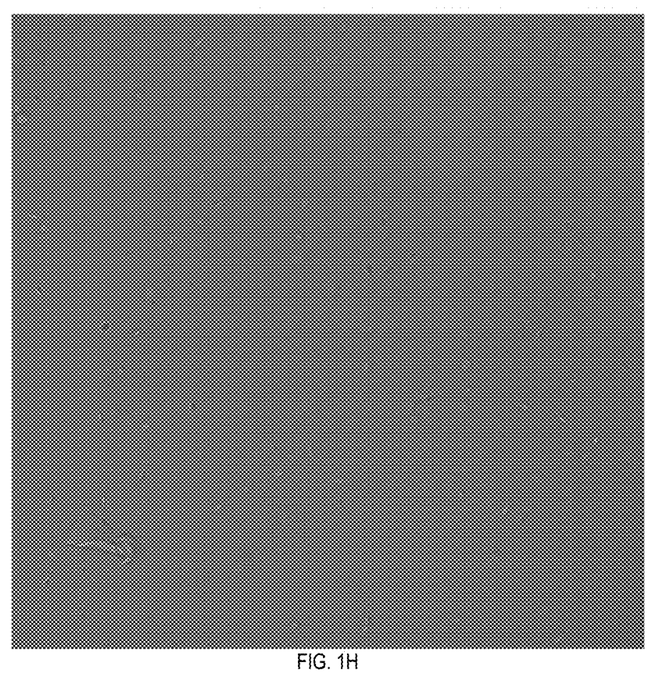
Figure 2A:
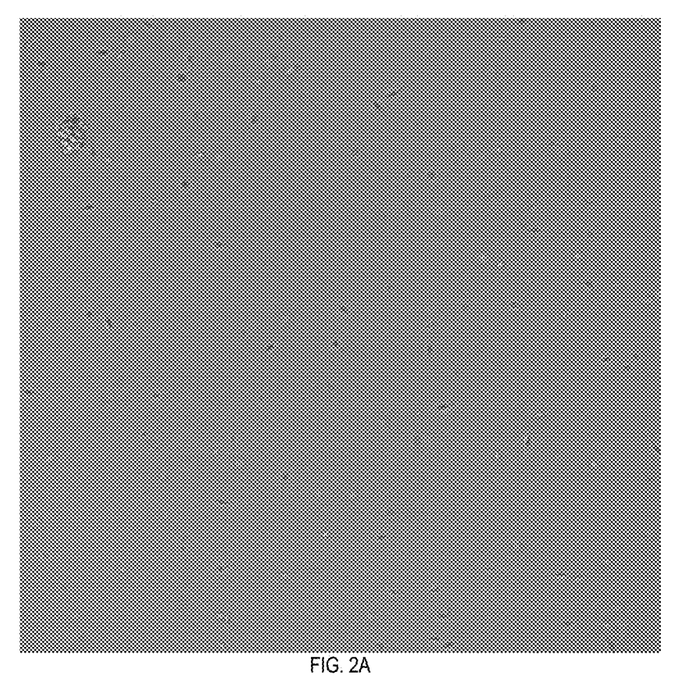
FIGS. 2A-2H depict photographs taken over about 9 seconds showing sperm processed with hydroxyurea (experimental).
Figure 2B:
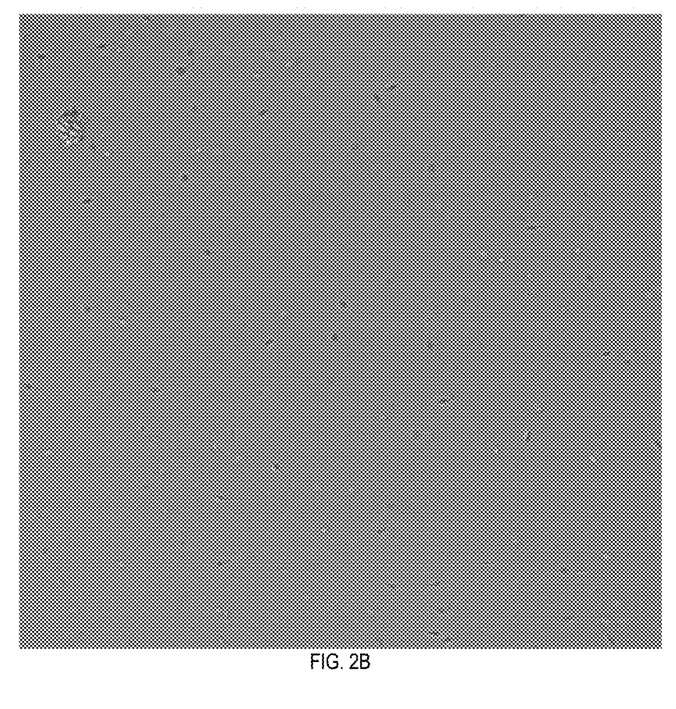
Figure 2C:
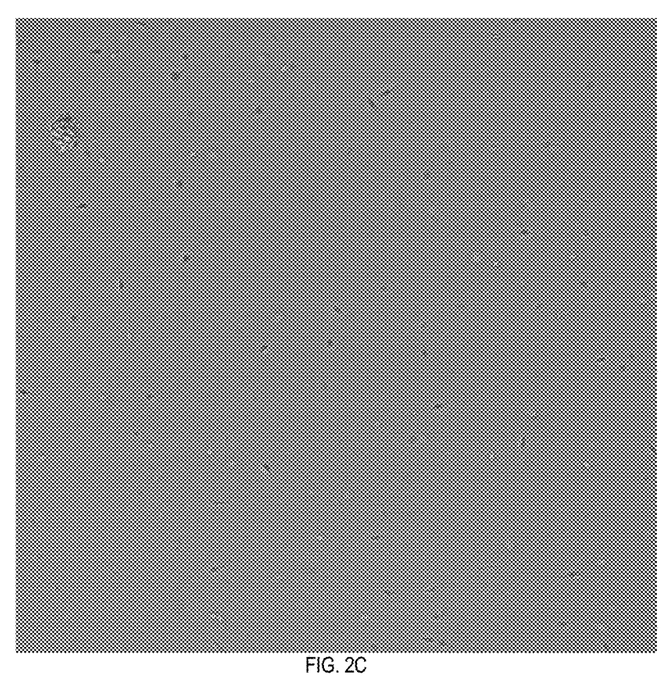
Figure 2D:
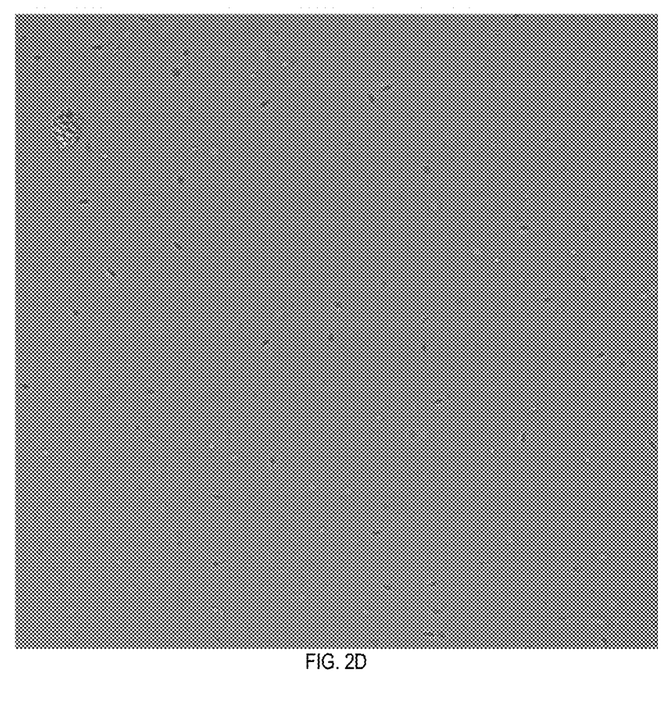
Figure 2E:
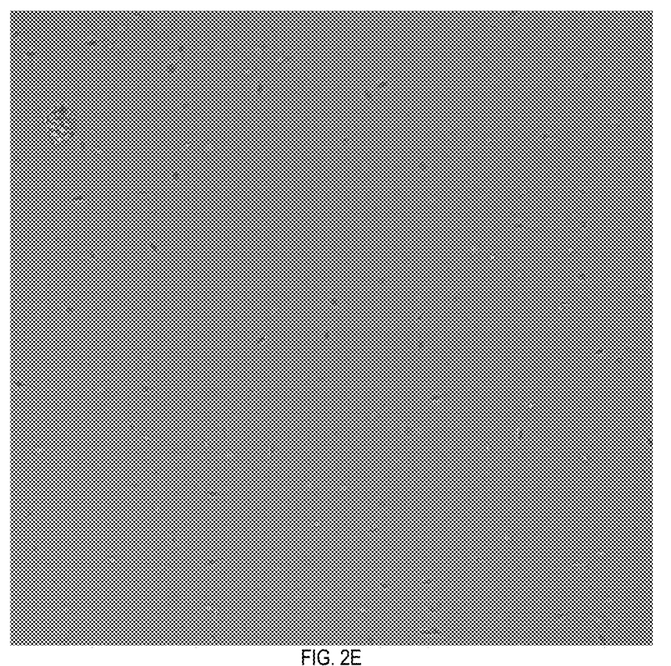
Figure 2F:
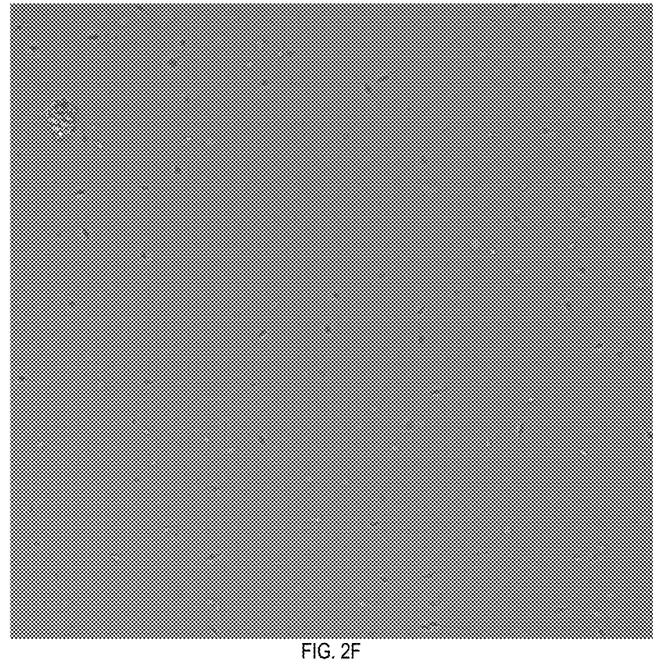
Figure 2G:
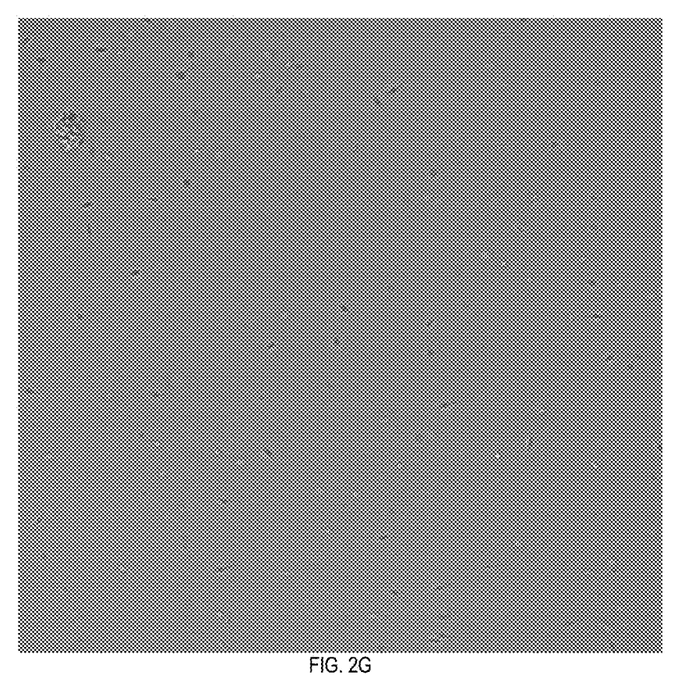
Figure 2H:
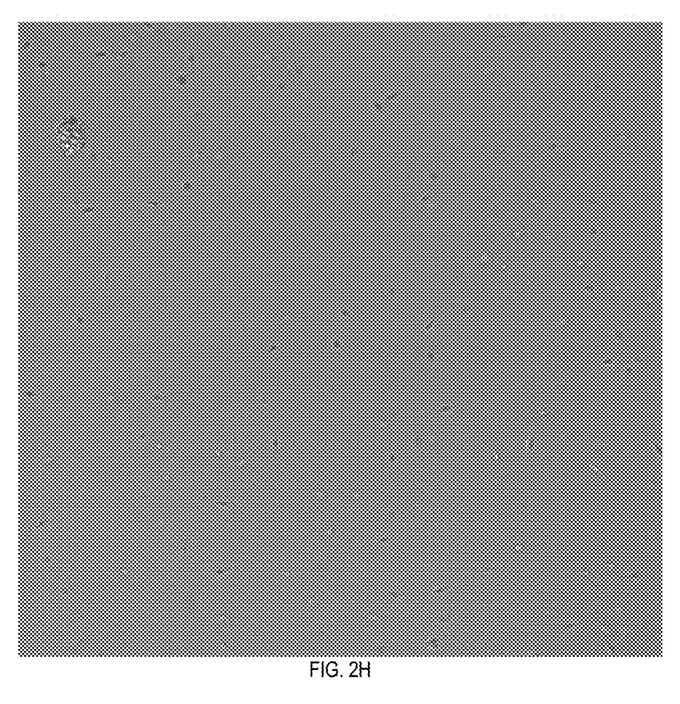

FIGS. 1A-1H and FIGS. 2A-2H demonstrate the effectiveness of HU at preserving, maintaining motility in, and maintaining survival of, motile spermatozoa that are subjected to cryopreservation. FIGS. 1A-1H illustrate still screens from a video showing non-HU treated (i.e., control) motile spermatozoa over about 9 seconds, with FIG. 1A corresponding to about 1 second elapsed, FIG. 1B corresponding to about 2 seconds elapsed, FIG. 10 corresponding to about 4 seconds elapsed, FIG. 1D corresponding to about 5 seconds elapsed, FIG. 1E corresponding to about 6 seconds elapsed, FIG. 1F corresponding to about 7 seconds elapsed, FIG. 1G corresponding to about 8 seconds elapsed, and FIG. 1H corresponding to about 9 seconds elapsed. As can be seen, a low level of overall spermatozoa with motility exists in the control group, with few, if any, spermatozoa exhibiting hyperactive motility. On the other hand, FIGS. 2A-2H illustrate still screens from a video showing HU treated (i.e., experimental) motile spermatozoa over about 9 seconds, with FIG. 2A corresponding to about 1 second elapsed, FIG. 2B corresponding to about 2 seconds elapsed, FIG. 2C corresponding to about 4 seconds elapsed, FIG. 2D corresponding to about 5 seconds elapsed, FIG. 2E corresponding to about 6 seconds elapsed, FIG. 2F corresponding to about 7 seconds elapsed, FIG. 2G corresponding to about 8 seconds elapsed, and FIG. 2H corresponding to about 9 seconds elapsed. As can be seen, a moderate to high level of overall spermatozoa with motility exists in the treatment group, with numerous spermatozoa exhibiting hyperactive motility as compared to the control group that has low post thaw motility.

These results of this Working Experiment 3 are significant, as they demonstrate that HU treatment is highly effective in preserving, or maintaining, the viability and motility of motile spermatozoa that have been subjected to cryopreservation. Moreover, HU treatment preserves or maintains the motility of motile spermatozoa at HU concentrations that are effective to inhibit HIV replication, such as in concentrations of 1 µM, as tested here. This dual feature (increasing motility while inhibiting HIV replication) of the HU described herein is an important aspect of the embodiments of this disclosure.

Working Example 4

Human sperm was processed with HU to show that HU is beneficial for maintaining motility of spermatozoa subjected to cryopreservation.

Post semen analysis was conducted of discarded and de-identified semen samples from Ovation Fertility Center that met the World Health Organization (WHO) criteria for normal semen samples. Those semen samples that met the WHO criteria for normal were divided into two halves. One half subjected to freezing with TEST-Yolk buffer (freezing buffer [FB]; Irvine Scientific, CA) containing 12% glycerol as cryoprotectant (control group). The remaining half of each sample was frozen with experimental freezing buffer composed of FB+HU (Sigma Aldridge, St. Louis; treatment group). Both control and experimental buffers were added on a 1:1 ratio to respective semen samples (v/v) in a dropwise manner. The final glycerol concentration in the semen+FB was 6% and the final HU concentration in semen+experimental freezing buffer was 1 µM to use a concentration of HU that is effective in inhibiting HIV replication. Pre-freeze sperm motility was determined for each sample prior to initiating the cooling arm of the freezing procedure. Samples in the control and treatment group were cooled for 24 hours to slow the HU induced vigorously motile cells in the treatment group. Subsequently, post cooling motility was determined prior to liquid nitrogen vapor phase freezing for 30 minutes before being stored immersed in LN for at least 24 hours before being thawed for analysis. Samples were thawed at room temperature for 35 minutes prior to motility analysis.

The results, as shown in Table 2, below, indicate that supplementation of freezing medium with HU maintained motility of the initial population of motile spermatozoa (pre-freeze) better than the control group, which did not contain HU.

TABLE 2

| Sample No. | Pre-cool Motility (Control; %) | Post-cool Motility (Control; %) | Post-thaw Motility/Survival Relative to Post-cool Motility (Control; %) | Pre-cool Motility (HU; %) | Post-cool Motility (HU; %) | Post-thaw Motility/Survival Relative to Post-cool Motility (HU; %) |
|---|---|---|---|---|---|---|
| 1 | 57 | 56 | 37/66 | 57 | 66 | 50/76 |
| 2 | 70 | 34 | 24/71 | 70 | 65 | 32/49 |
| 3 | 59 | 49 | 28/57 | 59 | 62 | 44/71 |

As can be seen above, HU treatment of motile spermatozoa positively effects post-thaw motility in spermatozoa that have been subjected to cryopreservation. It should be noted, however, that an experiment including a higher number of samples than was tested in Working Example 4 would provide for greater statistical accuracy. These results indicate that motile spermatozoa that are contacted with HU have a relatively greater post-thaw motility and survival rate when compared to the control group of motile spermatozoa.

Prophetic Example 5

It is believed that HU treated sperm is safe and effective for fertilization of an egg and subsequent zygote development (e.g., cleavage, compaction, cell division, blastulation, implementation, and embryogenesis). An experiment will be implemented, where samples of eggs, such as eggs from swine, bovine, or cricetinae (hamster) will be artificially fertilized (such as by IVF) with two sets of sperm samples, where one set has been treated with HU (experimental) and the other set has not been treated with HU (control). For example, if there are 20 samples of sperm, the 20 samples will be divided into two sets—20 samples for HU treatment and 20 control samples without HU treatment, such as by a buffer that does not contain HU. The sperm may be provided from an animal such as a swine, bovine, or cricetinae. The sets of sperm will then be used to fertilize eggs, preferably eggs from a single animal or a single animal per sample to minimize experimental variables. Subsequent development of the fertilized eggs of the sets of samples will be observed, measured, and recorded. By comparing development between the control and HU treated samples, it can be shown that sperm from HU treated semen samples are safe and effective for animal fertilization procedures and techniques.

It is to be understood that any given elements of the disclosed embodiments of the invention may be embodied in a single structure, a single step, a single substance or the like. Similarly, a given element of the disclosed embodiment may be embodied in multiple structures, steps, substances or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method of enhancing sperm motility, comprising:
providing a spermatozoon, and
contacting the spermatozoon with a composition comprising an effective amount of hydroxyurea.

2. The method of claim 1, wherein the composition is a buffer comprising human tubal fluid medium or modified human tubal fluid medium.

3. The method of claim 1, further comprising incubating the contacted spermatozoon for a period of between 1 minute and 24 hours.

4. The method of claim 1, wherein the hydroxyurea is present in the composition in an amount of from 0.1 µg/mL to 250 µg/mL.

5. The method of claim 1, wherein the enhancing sperm motility comprises activating sperm hyperactive motility.

6. The method of claim 1, wherein the hydroxyurea is present in the composition in an amount of from 10 µg/mL to 25 µg/mL.

7. The method of claim 1, wherein the spermatozoon is human spermatozoon.

8. The method of claim 1, wherein the spermatozoon is bovine spermatozoon.

9. The method of claim 1, further comprising incubating the contacted spermatozoon for a period of between 15 minutes and 3 hours.

10. The method of claim 1, further comprising washing the spermatozoon by centrifugation.

* * * * *